(12) United States Patent
Wiesner et al.

(10) Patent No.: US 7,915,228 B2
(45) Date of Patent: *Mar. 29, 2011

(54) DERIVATIVES OF ASIMADOLINE WITH COVALENTLY BONDED ACIDS

(75) Inventors: Matthias Wiesner, Seeheim-Jugenheim (DE); Christoph Seyfried, Seeheim-Jugenheim (DE)

(73) Assignee: Tioga Pharmaceuticals, Inc., San Diego, CA (US)

( * ) Notice: Subject to any disclaimer, the term of this patent is extended or adjusted under 35 U.S.C. 154(b) by 234 days.

This patent is subject to a terminal disclaimer.

(21) Appl. No.: 12/131,836

(22) Filed: Jun. 2, 2008

(65) Prior Publication Data

US 2008/0234209 A1    Sep. 25, 2008

Related U.S. Application Data

(63) Continuation of application No. 10/539,256, filed as application No. PCT/EP03/13206 on Nov. 25, 2003, now Pat. No. 7,385,065.

(30) Foreign Application Priority Data

Dec. 17, 2002   (EP) .................................... 10259245

(51) Int. Cl.
 *A61K 31/155*  (2006.01)
 *A61K 31/095*  (2006.01)
 *A61P 1/12*    (2006.01)
 *C07D 207/12*  (2006.01)

(52) U.S. Cl. ........... 514/27; 514/424; 548/556; 548/546
(58) Field of Classification Search ..................... 514/27, 514/424; 548/556, 546
 See application file for complete search history.

(56) References Cited

U.S. PATENT DOCUMENTS

| | | | |
|---|---|---|---|
| 4,760,069 | A | 7/1988 | Rzeszotarski et al. |
| 4,889,860 | A | 12/1989 | Rzeszotarski et al. |
| 5,532,266 | A | 7/1996 | Gottschlich et al. |
| 5,585,500 | A | 12/1996 | Drauz et al. |
| 5,776,972 | A | 7/1998 | Barber et al. |
| 6,060,504 | A | 5/2000 | Stein et al. |
| 6,191,126 | B1 | 2/2001 | Gamache |
| 6,303,611 | B1 | 10/2001 | Zhang et al. |
| 6,344,566 | B1 | 2/2002 | Bathe et al. |
| 6,569,449 | B1 | 5/2003 | Stinchcomb et al. |
| 2002/0025948 | A1 | 2/2002 | Banks et al. |
| 2003/0036546 | A1 | 2/2003 | Clemens |
| 2005/0176746 | A1 | 8/2005 | Weber et al. |
| 2006/0122255 | A1 | 6/2006 | Wiesner et al. |
| 2007/0179098 | A1 | 8/2007 | Wiesner et al. |

FOREIGN PATENT DOCUMENTS

| | | |
|---|---|---|
| DE | 4215213 | 11/1993 |
| DE | 19523502 | 1/1997 |
| DE | 19647538 | 5/1998 |
| EP | 0 569 802 | 11/1993 |
| JP | 09-020659 | 1/1997 |
| JP | 09-110830 | 4/1997 |
| JP | 2001-527062 | 12/2001 |
| WO | WO-99/33793 | 7/1999 |
| WO | WO-00/14065 | 3/2000 |
| WO | WO-01/98267 | 12/2001 |
| WO | WO-02/13801 | 2/2002 |
| WO | WO-02/58696 | 8/2002 |
| WO | WO-03/048113 | 6/2003 |
| WO | WO-03/097051 | 11/2003 |

OTHER PUBLICATIONS

Merck Manual Online Medical Library: The Merck Manual of Diagnosis and Therapy "Introduction: Pain"; also available at http://www.merck.com/mmpe/print/sec16/ch209/ch209a.html; last viewed Apr. 20, 2010.*
Merck Manual Online Medical Library: The Merck Manual for Healthcare Professionals "Pain"; also available at http://www.merck.com/mmpe/search.htm; last viewed Apr. 20, 2010.*
Camilleri, M., Neurogastroenterol Motil "Novel pharmacology: asimadoline, a kappa-opioid agonist, and visceral sensation", vol. 20, pp. 971-979 (2008).*
Wolff, M. E., Burger's Medicinal Chemistry and Drug Discovery, Fifth Edition, vol. 1: Principles and Practice, pp. 975-977 (Mar. 1995).*
Testa, Bernard, Biochemical Pharmacology "Prodrug resarch: futile or fertile?", vol. 68, pp. 2097-2106 (2004).*
Stella, V. J., Expert Opin. Ther. Patents "Prodrugs as therapeutics", vol. 14, issue 3, pp. 277-280 (2004).*
Ettmayer, Peter et al., Journal of Medicinal Chemistry "Lessons Learned from Marketed and Investigational Prodrugs", vol. 47, issue 10, pp. 2393-2404 (2004).*
Active ingredient [online], [retrieved on Nov. 22, 2006]. Retrieved from the Internet, URL; http://en.wikipedia.org/wiki/Active_pharmaceutical_ingredients>.
Cecil Textbook of Medicine, 20th ed. (1996) vol. 2, pp. 2050-2057.

(Continued)

*Primary Examiner* — Shaojia Anna Jiang
*Assistant Examiner* — Bahar Schmidtmann
(74) *Attorney, Agent, or Firm* — Morrison & Foerster LLP

(57) ABSTRACT

The present invention relates to derivatives of N-methyl-N-[(1S)-1-phenyl-2-((3S)-3-hydroxypyrrolidin-1-yl)ethyl]-2,2-diphenylacetamide with covalently bonded acids, and to the salts, solvates and prodrugs thereof, to the derivatives as medicaments, to the use of these derivatives for the preparation of a medicament, to the use of these derivatives for the preparation of a pharmaceutical composition, to a process for the preparation of the pharmaceutical compositions, to pharmaceutical compositions obtainable by this process, and to a process for the treatment of diseases which comprises the administration of the pharmaceutical composition.

23 Claims, No Drawings

OTHER PUBLICATIONS

Cecil Textbook of Medicine, 20th ed. (1996) vol. 2, pp. 1992-1996.
FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/indexhtml>.
OBACH, Drug-Drug Interactions: An Important Negative Attribute in Drugs. Drugs of Today (2003) 39:301-338.
*Lupus erythematosus* [online], [retrieved on Dec. 28, 2006]. Retrieved from the Internet, URL; http://en.wikipedia.org/wiki/Lupus_erythematosus>.
Lupus [online], [retrieved on Jul. 6, 2007]. Retrieved from the Internet, URL; http://www.nlm.nih.gov/medlineplus/lupus.html>.
Cancer [online], [retrieved on Jul. 6, 2007]. Retrieved from the Internet, URL; http://en.wikipedia.org/wiki/Cancer>.
Cancer [online], [retrieved on Jul. 6, 2007]. Retrieved from the Internet, URL; http://www.nlm.nih.gov/medlineplus/cancer.html>.
Irritable Bowel Syndrome: Tips on Controlling Your Symptoms [online], [retrieved on Jul. 6, 2007]. Retrieved from the Internet, URL; http://familydoctor.org/online/famdocen/home/common/digestive/disorders/112.html>.
Digestive Disorders [online], [retrieved on Jul. 6, 2007]. Retrieved from the Internet, URL; http://familydoctor.org/online/famdocen/home/common/digestive.html>.
Barber et al., British Journal of Pharmacology (Dec. 1994) 113(4):1317-1327.
Barber et al., Expert Opinion on Investigational New Drugs (1997) 6:1351-1368.
Gottschlich et al., Bioorganic & Medicinal Chemistry Letters (Jan. 1994) 4(5):677-682.
Hasler, "Disorders of Gastric Emptying," in Textbook of Gastroenterology, 3rd edition, Yamada (ed.), 1999, p. 1346.
Johnson, Medical Hypotheses (1995) 45(5):491-497.
Mendelson, American Journal of Psychiatry (2001) 158(6):963-964.
Morley et al., American Journal of Clinical Nutrition (1985) 42(6):1175-1178.
Quigley, Expert Opinion on Pharmacotherapy (2000) 1:881-887.
Non-Final Office Action from U.S. Appl. No. 09/647,813, mailed on Jun. 4, 2001.
Amendment from U.S. Appl. No. 09/647,813, filed Sep. 4, 2001.
Notice of Allowance from U.S. Appl. No. 09/647,813, mailed on Sep. 20, 2001.
Restriction Requirement from U.S. Appl. No. 10/514,887, mailed on Jan. 19, 2006.
Amendment in Response to Non-Final Office Action from U.S. Appl. No. 10/514,887, filed May 19, 2006.
Restriction Requirement from U.S. Appl. No. 10/514,887, mailed on Jun. 30, 2006.
Response to Restriction Requirement from U.S. Appl. No. 10/514,887, filed Jul. 31, 2006.
Non-Final Office Action from U.S. Appl. No. 10/514,887, mailed on Sep. 12, 2006.
Amendment in Response to Non-Final Office Action from U.S. Appl. No. 10/514,887, filed Dec. 12, 2006.
Final Rejection from U.S. Appl. No. 10/514,887, mailed on Mar. 8, 2007.
Amendment After Final Action Under 37 CFR § 1.116, from U.S. Appl. No. 10/514,887, filed Sep. 10, 2007.
Notice of Allowance for U.S. Appl. No. 10/539,256, mailed on Feb. 19, 2008, 9 pages.
Non-Final Office Action from U.S. Appl. No. 11/732,309, mailed on Nov. 27, 2007.
Amendment in Response to Non-Final Office Action from U.S. Appl. No. 11/732,309, filed May 27, 2008.
Non-Final Office Action for U.S. Appl. No. 11/732,309, mailed on May 13, 2009, 12 pages.
Nolen et al., Pharmaceutical Research (1994) 11(12):1707-1711.
Nolen et al., Biopharmaceuticals & Drug Disposition (1997) 18(8):681-695.
Notificaiton of Reasons for Refusal (translation) for JP 2004-559717, mailed May 11, 2010, 3 pages.
Wermuth, The Practice of Medicinal Chemistry, Technomics, Inc. (1999) p. 276.

* cited by examiner

DERIVATIVES OF ASIMADOLINE WITH COVALENTLY BONDED ACIDS

CROSS-REFERENCE TO RELATED APPLICATIONS

This application is a continuation of U.S. application Ser. No. 10/539,256 filed Jun. 16, 2005 which is a national phase of PCT Application No. PCT/EP2003/013206 internationally filed Nov. 25, 2003, which claims priority from European Patent Office Application No. 10259245.4 filed Dec. 17, 2002. The contents of these documents are incorporated herein by reference in their entirety.

The present invention relates to derivatives of N-methyl-N-[(1S)-1-phenyl-2-((3S)-3-hydroxypyrrolidin-1-yl)ethyl]-2,2-diphenylacetamide with covalently bonded acids, to these derivatives as medicaments, to the use of these derivatives for the preparation of a medicament, to the use of these derivatives for the preparation of a pharmaceutical composition, to a process for the preparation of the said pharmaceutical compositions, to pharmaceutical compositions obtainable by this process, and to a process for the treatment of diseases which comprises the administration of the said pharmaceutical composition.

The compound N-methyl-N-[(1S)-1-phenyl-2-((3S)-3-hydroxypyrrolidin-1-yl)ethyl]-2,2-diphenylacetamide and in particular the hydrochloride (EMD 61753) is known, for example under the name asimadoline, and has already been described in EP-A-0 569 802 (U.S. Pat. No. 5,532,226), EP-A-0 752 246 (U.S. Pat. Nos. 5,776,972 and 5,977,161), DE-A-198 49 650, EP-A-0 761 650 (U.S. Pat. No. 6,060,504) and EP-A-1 073 634 (U.S. Pat. No. 6,344,566). The hydrochloride of this compound can be employed as a medicament active ingredient and exhibits a number of advantageous properties in various indications.

The invention had the object of finding novel stable derivatives of N-methyl-N-[(1S)-1-phenyl-2-((3S)-3-hydroxypyrrolidin-1-yl)ethyl]-2,2-diphenylacetamide which have better solubility, better absorption, greater stability, lower hygroscopy and/or improved pharmacokinetic properties.

Surprisingly, novel derivatives of N-methyl-N-[(1S)-1-phenyl-2-((3S)-3-hydroxypyrrolidin-1-yl)ethyl]-2,2-diphenylacetamide have now been found which exhibit advantageous properties compared with the known administration forms, in particular compared with N-methyl-N-[(1S)-1-phenyl-2-((3S)-3-hydroxypyrrolidin-1-yl)ethyl]-2,2-diphenylacetamide, hydrochloride, as medicament active ingredient for a multiplicity of indications. The advantageous properties of the derivatives according to the invention preferably include improved solubility behaviour, modified, in particular improved pharmacokinetic behaviour, a modified toleration profile and/or a modified half-value time, preferably an extended half-value time.

Surprisingly, the derivatives according to the invention interact intensively with the enterohepatic circulation. Thus, derivatives according to the invention can be cleaved, derivatised and/or additionally metabolised by interactions with the enterohepatic circulation or formed from free N-methyl-N-[(1S)-1-phenyl-2-((3S)-3-hydroxypyrrolidin-1-yl)ethyl]-2,2-diphenylacetamide. Furthermore, a derivative according to the invention can be converted into another derivative according to the invention by interactions with the enterohepatic circulation. It is assumed that at least some of the advantageous properties of the derivatives according to the invention arise due to interactions between a derivative according to the invention and the enterohepatic circulation.

The present invention therefore relates to derivatives of N-methyl-N-[(1S)-1-phenyl-2-((3S)-3-hydroxypyrrolidin-1-yl)ethyl]-2,2-diphenylacetamide with at least one covalently bonded acid. This invention likewise relates to the salts, solvates and prodrugs of the derivatives of N-methyl-N-[(1S)-1-phenyl-2-((3S)-3-hydroxypyrrolidin-1-yl)ethyl]-2,2-diphenylacetamide with at least one covalently bonded acid. For the purposes of the invention, covalently bonded acid means that the derivative of N-methyl-N-[(1S)-1-phenyl-2-((3S)-3-hydroxypyrrolidin-1-yl)ethyl]-2,2-diphenylacetamide contains at least one acid, or a radical derived from an acid, which is not bonded to the N-methyl-N-[(1S)-1-phenyl-2-((3S)-3-hydroxypyrrolidin-1-yl)-ethyl]-2,2-diphenylacetamide by an ionic interaction, in particular by salt formation. The derivative according to the invention preferably comprises at least one acid, or a radical derived from an acid, which is bonded to the N-methyl-N-[(1S)-1-phenyl-2-((3S)-3-hydroxypyrrolidin-1-yl)ethyl]-2,2-diphenylacetamide by esterification or etherification.

The acid or the radical derived from an acid is preferably bonded to the N-methyl-N-[(1S)-1-phenyl-2-((3S)-3-hydroxypyrrolidin-1-yl)ethyl]-2,2-diphenylacetamide via the 3-hydroxypyrrolidine group of the N-methyl-N-[(1S)-1-phenyl-2-((3S)-3-hydroxypyrrolidin-1-yl)ethyl]-2,2-diphenylacetamide.

Particular preference is therefore given to derivatives according to the invention in which the acid or the radical derived from an acid is covalently bonded to the N-methyl-N-[(1S)-1-phenyl-2-((3S)-3-hydroxypyrrolidin-1-yl)-ethyl]-2,2-diphenylacetamide by esterification or etherification with the 3-hydroxypyrrolidine group. N-methyl-N-[(1S)-1-phenyl-2-((3S)-3-hydroxypyrrolidin-1-yl)ethyl]-2,2-diphenylacetamide has a free hydroxyl function in the 3-position of the pyrrolidine group and is therefore an alcohol. The derivatives according to the invention are therefore preferably the esters or ethers of N-methyl-N-[(1S)-1-phenyl-2-((3S)-3-hydroxypyrrolidin-1-yl)ethyl]-2,2-diphenylacetamide, and very particularly preferably the esters or ethers of N-methyl-N-[(1S)-1-phenyl-2-((3S)-3-hydroxypyrrolidin-1-yl)ethyl]-2,2-diphenylacetamide with one of the acids listed below.

For the purposes of this invention, acids are, for example, inorganic acids, preferably inorganic oxygen acids, such as the oxygen acids of the halogens, of sulfur, of nitrogen and of phosphorus, particularly preferably chloric acid, sulfurous acid, sulfuric acid, sulfamic acid, nitrous acid, nitric acid, phosphoric acids, preferably orthophosphoric acid, and organic acids, preferably aliphatic, alicyclic, araliphatic, aromatic or heterocyclic monobasic or polybasic carboxylic, sulfonic or sulfuric acids, particularly preferably methane- or ethanesulfonic acid, ethanedisulfonic acid, 2-hydroxyethanesulfonic acid, benzenesulfonic acid, p-toluenesulfonic acid, naphthalenemono- and -disulfonic acids and laurylsulfuric acid, very particularly preferably mono- or polybasic carboxylic acids and mono- or polybasic hydroxycarboxylic acids, such as formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, glucuronic acid, galacturonic acid, ascorbic acid, nicotinic acid and isonicotinic acid.

The acid is preferably selected from physiologically tolerated acids, in particular from the physiologically tolerated acids of the above-mentioned acids.

The acid is particularly preferably selected from carboxylic acids, hydroxycarboxylic acids and inorganic oxygen acids, very particularly preferably from hydroxycarboxylic acids and inorganic oxygen acids.

The carboxylic acids are preferably selected from mono- or polybasic carboxylic acids, preferably mono- or dibasic carboxylic acids, having from 1 to 12 carbon atoms, preferably from 1 to 6 carbon atoms, such as the monocarboxylic acids formic acid, acetic acid, propionic acid, diethylacetic acid, pivalic acid, nicotinic acid and isonicotinic acid, and the dicarboxylic acids malonic acid, succinic acid, pimelic acid, fumaric acid and maleic acid. The carboxylic acid is preferably acetic acid.

The hydroxycarboxylic acids are preferably selected from monohydroxymonocarboxylic acids, such as lactic acid, monohydroxydi- or -polycarboxylic acids, such as malic acid and citric acid, and polyhydroxymonocarboxylic acids, such as sugar acids, in particular ascorbic acid, glucuronic acid and galacturonic acid.

The inorganic oxygen acids are preferably selected from sulfuric acid, orthophosphoric acid and nitric acid, preferably sulfuric acid and orthophosphoric acid and in particular sulfuric acid.

Particular preference is given to derivatives according to the invention which contain at least one free acid group, i.e. an acid function which is capable of salt formation or is in the form of a salt.

A preferred embodiment of the present invention therefore relates to derivatives according to the invention in which the acid is selected from dibasic carboxylic acids, monobasic hydroxycarboxylic acids and at least dibasic inorganic oxygen acids, in particular from the dibasic carboxylic acids, monobasic hydroxycarboxylic acids and at least dibasic inorganic oxygen acids mentioned above as preferred.

A particularly preferred embodiment of the present invention relates to derivatives according to the invention in which the monobasic hydroxycarboxylic acid is selected from sugar acids and is in particular glucuronic acid.

A further particularly preferred embodiment of the present invention relates to derivatives according to the invention in which the dibasic inorganic oxygen acid is sulfuric acid.

A particularly preferred embodiment of the present invention relates to derivatives according to the invention in which the acid is selected from glucuronic acid and sulfuric acid.

The derivatives according to the invention are preferably selected from the esters of the above-mentioned monocarboxylic acids with N-methyl-N-[(1S)-1-phenyl-2-((3S)-3-hydroxypyrrolidin-1-yl)ethyl]-2,2-diphenylacetamide as alcohol component, the esters of the above-mentioned inorganic oxygen acids with N-methyl-N-[(1S)-1-phenyl-2-((3S)-3-hydroxypyrrolidin-1-yl)ethyl]-2,2-diphenylacetamide as alcohol component and the ethers of the above-mentioned hydroxycarboxylic acids with N-methyl-N-[(1S)-1-phenyl-2-((3S)-3-hydroxypyrrolidin-1-yl)ethyl]-2,2-diphenylacetamide as second alcohol component.

In the case of polybasic acid esters according to the invention, the monoesters are generally preferred. In the case of polyhydroxycarboxylic acid ethers according to the invention, the monoethers are generally preferred. In general, the N-methyl-N-[(1S)-1-phenyl-2-((3S)-3-hydroxypyrrolidin-1-yl)-ethyl]-2,2-diphenylacetamide derivatives according to the invention and hydroxycarboxylic acids are essentially neither in the form of mixed esters and ethers of a hydroxycarboxylic acid, nor in the form of a mixture of two derivatives in which some of the N-methyl-N-[(1S)-1-phenyl-2-((3S)-3-hydroxypyrrolidin-1-yl)ethyl]-2,2-diphenylacetamide is bonded to the hydroxycarboxylic acid in the form of an ether and some of the N-methyl-N-[(1S)-1-phenyl-2-((3S)-3-hydroxypyrrolidin-1-yl)ethyl]-2,2-diphenylacetamide is bonded to the hydroxycarboxylic acid in the form of an ester.

Particularly preferred derivatives according to the invention are therefore those which comprise at least 40% by weight, preferably at least 60% by weight, particularly preferably at least 70% by weight, very particularly preferably at least 80% by weight or at least 90% by weight, at most 100% by weight, but in many cases less than 100% by weight, for example from 60 to 90% by weight, from 70 to 95% by weight, from 80 to 99.9% by weight or from 90 to 100% by weight, of a single, defined compound, which preferably comprises only one molecule or unit of N-methyl-N-[(1S)-1-phenyl-2-((3S)-3-hydroxypyrrolidin-1-yl)ethyl]-2,2-diphenylacetamide as alcohol component and one molecule or unit of an acid, preferably one of the above-mentioned acids, in covalently bonded form.

Examples of preferred derivatives according to the invention are compounds of the formula I

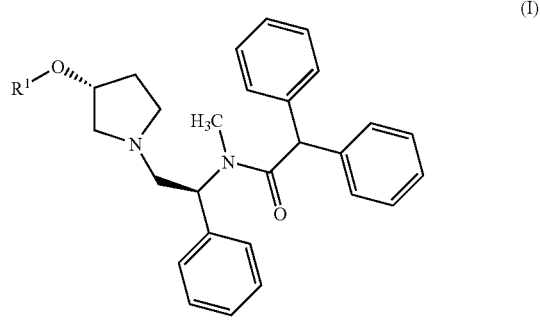

(I)

in which $R^1$ is selected from a) acyl radicals having from 1 to 12, preferably from 1 to 6, carbon atoms, preferably alkanoyl radicals having from 1 to 12, preferably from 1 to 6, carbon atoms and particularly preferably formyl, acetyl, propionyl, isopropionyl, butyryl, isobutyryl and pivaloyl, in particular acetyl;

b) acyl radicals having from 1 to 12, preferably from 1 to 6, carbon atoms which contain one hydroxyl group and/or one or more carboxyl groups, and particularly preferably selected from

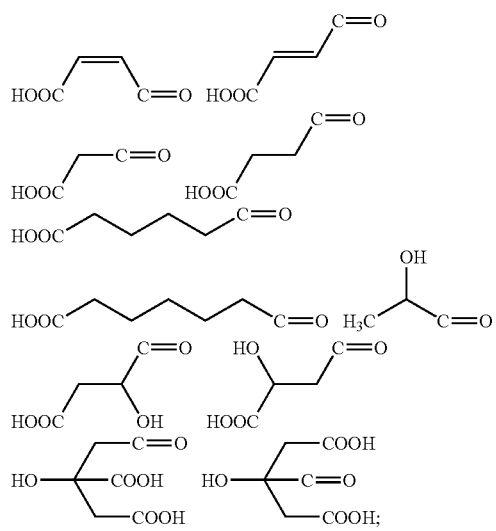

c) alkyl radicals derived from polyhydroxymonocarboxylic acids by removal of a hydroxyl group, preferably from ascorbic acid, glucuronic acid and galacturonic acid, particularly preferably and/or the open-chain forms thereof;
and from
d) sulfonic acid groups derived from sulfuric acid by removal of a hydroxyl group, phosphonic acid groups derived from orthophosphoric acid by removal of a hydroxyl group, and nitro groups derived from nitric acid by removal of a hydroxyl group, in particular

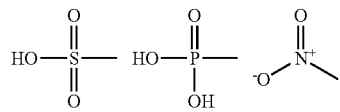

and the salts and solvates thereof.

In the radicals $R^1$ reproduced under c) and d), the free bond or the free valence preferably symbolises, for reasons of clarity, the point where $R^1$ in the formula I is bonded to the oxygen atom. In the radicals $R^1$ reproduced under c), the solid wedge preferably symbolises a bond which points upwards with respect to the plane of the paper. In the radicals $R^1$ reproduced under c), the hatched wedge preferably symbolises a bond which points downwards with respect to the plane of the paper.

Particularly preferred derivatives according to the invention are selected from compounds of the formula Ia

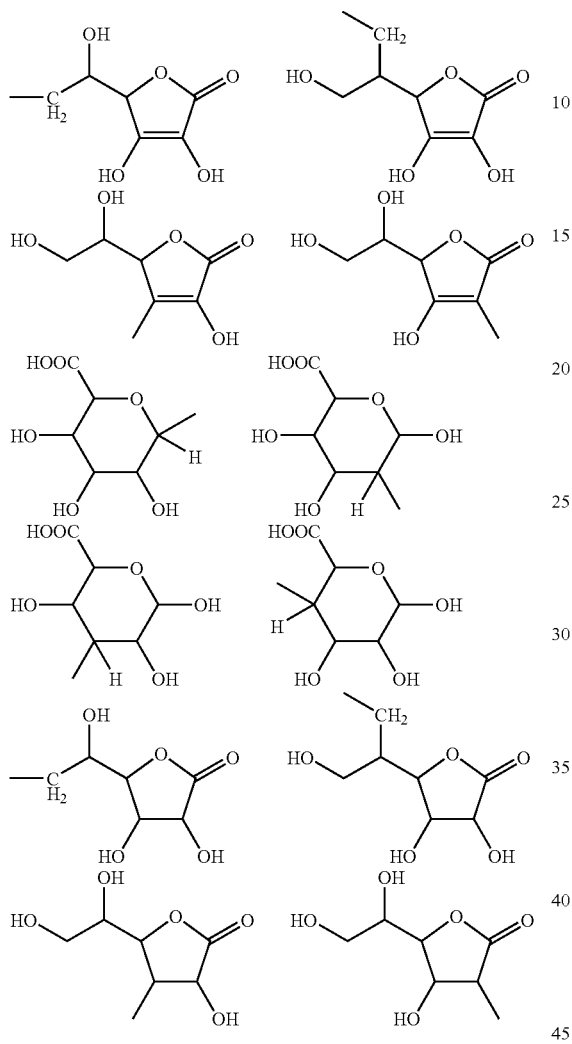

very particularly preferably

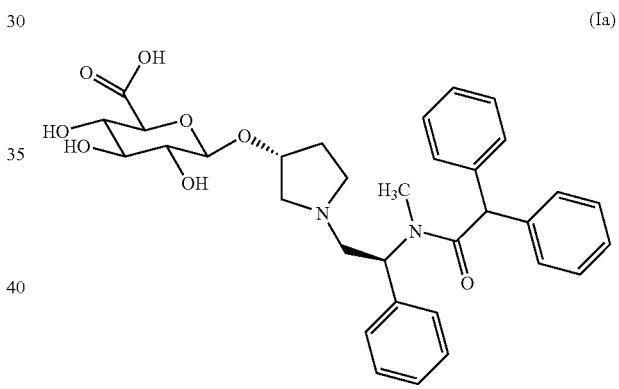

(Ia)

(6-((1S)-1-{[(2,2-diphenylethanoyl)methylamino]phenylethyl}-(3S)-pyrrolidin-3-yloxy)-D-glucuronic acid)
and compounds of the formula Ib

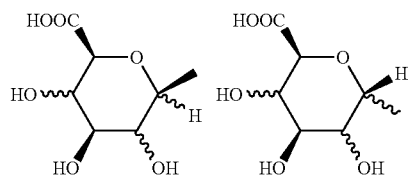

and in particular

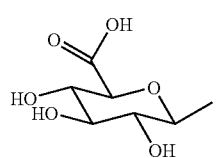

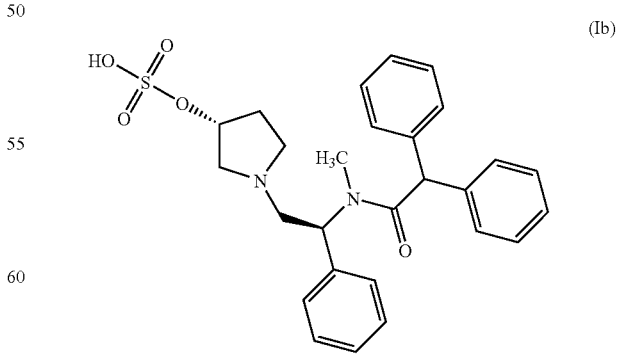

(Ib)

(mono-((1S)-1-{[(2,2-diphenylethanoyl)methylamino]phenylethyl}-(3S)-pyrrolidin-3-yl) sulfate)
and the salts and solvates thereof.

Preference is furthermore given to compounds of the formula (Ic)

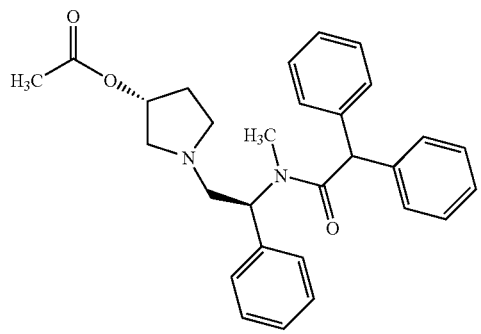

(Ic)

(N-methyl-N-[(1S)-1-phenyl-2-((3S)-3-acetoxypyrrolidin-1-yl)ethyl]-2,2-diphenylacetamide)

and the salts and solvates thereof.

The invention also relates to pharmaceutically tolerated derivatives of the compounds according to the invention, in particular prodrugs and prodrug derivatives, salts and solvates of the compounds according to the invention, in particular of the compounds of the formula I and sub-formulae thereof.

The invention also relates to the optically active forms (stereoisomers), preferably the enantiomers, the racemates and the diastereomers, and the hydrates and solvates of the compounds according to the invention. The term solvates of the compounds according to the invention is taken to mean adductions of inert solvent molecules onto the compounds according to the invention which form owing to their mutual attractive force. Solvates are, for example, mono- or dihydrates or alcoholates.

The term prodrugs of compounds according to the invention is taken to mean derivatives according to the invention which have been modified by means of additional groups or contain additional groups. Preference is given to compounds of the formula I which have been modified by means of additional groups, for example alkyl or acyl groups, sugars or oligopeptides and which are rapidly cleaved in the organism to give the active compounds according to the invention. These also include biodegradable polymer derivatives of the compounds according to the invention, as described, for example, in Int. J. Pharm. 115, 61-67 (1995). Examples of prodrug derivatives of this type are the alkyl esters of derivatives according to the invention which contain at least one free acid group and the esters of derivatives according to the invention which contain at least one free hydroxyl group.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

Of the pharmaceutically tolerated derivatives, preference is given to the salts and solvates of derivatives according to the invention, in particular the derivatives of the formula I according to the invention, and in particular the physiologically tolerated salts and solvates thereof.

A derivative according to the invention and in particular a compound of the formula I can be converted into a salt by the action of an acid or base. Thus, a derivative according to the invention, in particular a basic derivative according to the invention, can be converted into the associated acid-addition salt by means of an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids and laurylsulfuric acid. Salts with physiologically unacceptable acids, for example picrates, can be used for the isolation and/or purification of the derivatives according to the invention.

The acid employed for the formation of the acid-addition salt may be identical to or different from the acid covalently bonded in the derivatives according to the invention, but the acid employed for the formation of the acid-addition salt is not covalently bonded in the salt (acid-addition salt), but instead is associated by ionic interactions. However, the acid covalently bonded in the derivative according to the invention is preferably different from the acid used for the formation of the acid-addition salt. If a derivative according to the invention is in the form of a salt and in particular in the form of a physiologically tolerated salt, this is generally an acid-addition salt and in particular a physiologically tolerated acid-addition salt.

If the acid covalently bonded in the derivative according to the invention contains one or more free acid groups, the derivative according to the invention may be in the salt form as a so-called internal salt through internal salt formation, even without addition of an acid or base. If the acid covalently bonded in the derivative according to the invention is a physiologically tolerated acid and contains one or more free acid groups, the derivative according to the invention may be in the form of a physiologically tolerated salt through internal salt formation, even without addition of an acid or base.

Alternatively, a derivative according to the invention, in particular an acidic derivative according to the invention, can be converted into the base-addition salt by means of a base, for example by reaction of equivalent amounts of a derivative according to the invention and of a base in an inert solvent, such as ethanol, followed by evaporation. Suitable bases for this reaction are, in particular, those which give physiologically acceptable salts. Suitable bases are known to the person skilled in the art. For example, derivatives according to the invention can be converted into the corresponding metal salts, in particular alkali metal salts or alkaline earth metal salts, or into the corresponding ammonium salts, by means of bases, such as amines, alkali metal hydroxides, alkaline earth metal hydroxides, alkali metal carbonates and alkaline earth metal carbonates, preferably sodium hydroxide, potassium hydroxide, sodium carbonate or potassium carbonate. It is also possible to use physiologically acceptable organic bases, such as, for example, ethanolamine.

The present invention preferably relates to the derivatives according to the invention in isolated and/or essentially pure form. Essentially pure preferably means that the derivatives according to the invention have in a purity of greater than 60% by weight, preferably greater than 80% by weight, particularly preferably greater than 90% by weight and in particular greater than 95% by weight, such as, for example, greater than 97% by weight, greater than 99% by weight, greater than 99.9% by weight, greater than 99.99% by weight, or have a purity of up to 100% by weight. In mixtures of derivatives according to the invention, the purity data preferably relate to the respective derivative and in particular to the derivatives according to the invention present as principal constituents. In this connection, principal constituents preferably denotes the derivatives according to the invention present in the mixture which are present in the greatest proportion, where the proportion of a principal constituent in the mixture is preferably at least 10% by weight, preferably at least 30% by weight, particularly preferably at least 60% by weight and in particular at least 80% by weight, but less than 100% by weight, based on the total weight of the derivatives according to the invention present.

The derivatives according to the invention and/or the salts and solvates thereof exhibit a number of valuable pharmacological properties. Thus, they preferably exhibit analgesic, neuroprotective, antiinflammatory, antiasthmatic, diuretic, anticonvulsive and/or antitussive actions, antagonise hyperalgesia, in particular inflammation-induced hyperalgesia, protect against and are suitable for the treatment of conditions of pain, cerebral oedema, conditions of undersupply of the central nervous system and in particular hypoxia, and for the treatment and amelioration of the secondary damage after ischaemia, as described, for example, in EP-A-0 569 802, the disclosure content of which is expressly incorporated herein by way of reference. Thus, experiments have shown that the compounds according to the invention act on mice or rats in the "writhing test" (method, cf. Siegmund et al., Proc. Soc. Exp. Biol. 95, (1957), 729-731). The analgesic action as such can furthermore be demonstrated in the "tail-flick test" on mice or rats (method, cf. d'Amour and Smith, J. Pharmacol. Exp. Ther. 72, (1941), 74-79), furthermore in the "hot plate test" (cf. Schmauss and Yaksh, J. Pharmacol. Exp. Ther. 228, (1984), 1-12 and the literature cited therein). Particularly strong actions can be observed in rats in the model of carrageenan-induced hyperalgesia (cf. Bartoszyk and Wild, Neuroscience Letters 101 (1989) 95). At the same time, the compounds exhibit no or only a slight tendency towards physical dependency. In addition, corresponding experiments carried out by customary methods have demonstrated the pronounced antiinflammatory, diuretic, anticonvulsive and neuroprotective actions. The derivatives according to the invention exhibit high affinity with respect to the binding behaviour to kappa-receptors.

A particular aspect of the present invention relates to the efficacy of the derivatives according to the invention for the prophylaxis and/or treatment of functional gastrointestinal diseases, also called functional gastric and/or intestinal diseases below or functional gastric/intestinal diseases for short. The group of functional gastrointestinal diseases is described in detail and classified in GUT: Rome II: A Multinational consensus Document on Functional Gastrointestinal Disorders, Supplement II, Vol 45, 1999, the disclosure content of which is expressly incorporated herein by way of reference.

The functional gastrointestinal diseases are preferably selected from functional gastroduodenal diseases, of which preferably functional nausea and particularly preferably dyspepsia, in particular dyspepsia not associated with an ulcer; functional intestinal diseases, of which preferably functional abdominal pain, preferably functional wind or flatulence, particularly preferably functional obstipation, constipation or blockage, likewise particularly preferably functional diarrhea, and in particular irritable bowel, irritable colon or IBS (irritable bowel syndrome); and chronic motility disorders.

The efficacy of the derivatives according to the invention in the said indications or clinical pictures can be determined using standard methods known from the prior art, or methods analogous thereto. The indications and methods for the determination of the efficacy in these indications are described, for example, in N. J. Talley, V. Stanghellini, R. C. Heading, K. L. Koch, J. R. Malagelada, G. N. J. Tytgat; Gut 1999; 45 (Suppl 2): II37-II42; W. G. Thompson, G. F. Longstreth, D. A. Drossman, K. W. Heaton, E. J. Irvine, S. A. Müller-Lissner; Gut 1999; 45 (Suppl 2): II43-II47; S. J. O. Veldhuyzen van Zanten, N. J. Talley, P. Bytzer, K. B. Klein, P. J. Whorwell, A. R. Zinsmeister; Gut 1999; 45 (Suppl 2): II69-II77; M. Dapoigny, M. Homerin, B. Scherrer, B. Fraitag; Gut (34, Suppl. 3, S30, 1993); J.-L. Abitbol, B. Scherrer, C. de Meynard, G. Meric, B. Fraitag, Gut (39, Suppl. 3, A229-A230, 1996); and N. J. Talley, S. V. Van Zanten, L. R. Saez, G. Dukes, T. Perschy, M. Heath, C. Kleoudis, A. W. Mangel; Alimentary Pharmacology and Therapeutics 15: 4, 525-537; the disclosure content of which is incorporated in full by way of reference.

The present invention therefore also relates to the use of the derivatives according to the invention for the diagnosis, prophylaxis and/or treatment of functional gastrointestinal diseases.

The present invention therefore preferably also relates to the use of the derivatives according to the invention for the preparation of a medicament for the diagnosis, prophylaxis and/or treatment of functional gastrointestinal diseases.

In contrast to other compounds having a similar activity spectrum, the derivatives according to the invention are, in particular, particularly suitable for the treatment of inflammatory intestinal diseases and for use in pharmaceutical preparations for the treatment of inflammatory intestinal diseases since, besides the analgesic and antiinflammatory action, they are suitable for normalising the intestinal motor system impairments caused by the disease. In particular, they are suitable for restarting intestinal movements if there is a risk of intestinal obstruction due to the inflammatory intestinal disease, or it has already occurred. This action can also be employed for the treatment of postoperative ileus and the pain associated therewith. Inflammatory intestinal diseases frequently result in colonalgia, digestive disorders and in the worst case intestinal obstruction. In particular, the latter is often associated with colic-like pain as a consequence of a strong contraction stimulus, retention of faeces and flatus, vomiting and, with increasing duration of the condition, dehydration, abdominal resistance and finally shock. The derivatives according to the invention can advantageously be employed for the treatment and amelioration of the abovementioned diseases or symptoms. In particular, they ameliorate the pain associated with inflammatory intestinal diseases and, in the acute case of an intestinal blockage threatened or caused by the inflammatory intestinal disease, can re-normalise or restart the intestinal motor system without causing detectable side effects, as described, for example, in EP-A-0 752 246, the disclosure content of which is expressly incorporated herein by way of reference.

The use of the derivatives according to the invention for the treatment and/or prophylaxis of inflammatory intestinal diseases and in particular the use of the derivatives according to the invention for the preparation of a medicament for the treatment and/or prophylaxis of inflammatory intestinal diseases is therefore a preferred aspect of the present invention.

The present invention also relates to the use of the derivatives according to the invention for the preparation of a medicament for the diagnosis, prophylaxis and/or treatment of neuropathy, the clinical pictures and symptoms associated therewith and the diseases related thereto.

Neuropathy, or peripheral neuropathy, is a generally known term relating to diseases of the peripheral nerves, usually nerve damage.

The peripheral nerve system consists of nerves which branch out of the spinal cord into all parts of the body. Nerve damage occurring in only one part of the body is known as mononeuropathy, nerve damage in a number of areas as polyneuropathy. Radiculitis denotes neuropathy relating to the nerve roots. If the disease occurs symmetrically on both sides of the body, the state is referred to as symmetrical neuropathy. Peripheral neuropathy can occur as a consequence of diabetes, vitamin deficiency, HIV, cancer, viral diseases, alcohol abuse or as side effect of pharmaceuticals. It can therefore also be categorised by cause, such as, for example, as diabetic neuropathy, food-induced neuropathy or alcohol-induced neuropathy. If a cause cannot be determined, the state is called idiopathic neuropathy. Peripheral neuropathies are widespread, frequently have a considerable adverse effect on the general state of health of the patient and not infrequently result in disabilities. The aetiology, the clinical picture, the occurrence and/or the interactions with other diseases have been discussed in detail in the literature, for example in Boulton, Diabetes Metab 1998; 24 (Suppl 3): 55-65; IIIa, Eur Neurol 1999; 41 (Suppl 1): 3-7; Lagueny, Rev Prat 2000; 50: 731-735; Peltier and Russell, Curr Opin Neurol 2002; 15: 633-638; Simpson, J Neurovirol 2002; 8 (Suppl 2): 33-41; Sweeney, Clin J Oncol Nurs 2002; 6: 163-166; and Wulff and Simpson, Semin Neurol 1999; 19: 157-164). The disclosure content of the said publications and the references cited therein is expressly incorporated herein by way of reference.

The most widespread complication of diabetes is neuropathy. It is estimated that up to 60 percent of diabetes patients develop neuropathy as a consequence of diabetes. Neuropathy is typically associated with a wide range of symptoms, inter alia numbness or tingling, very unpleasant pins and needles sensation, the feeling of receiving a series of electric shocks, and pain of various types and severity. These symptoms may occur individually or in combination.

The symptoms of diabetic neuropathy and in particular the pain associated therewith usually relates to the feet and ankles and to a lesser extent the legs above the knee and the arms. Inadequate setting of the blood sugar level regularly results in nerve damage, which in turn results, with fair certainty, in the development of the clinical picture of diabetic neuropathy. The trigger of diabetic neuropathy is known, namely diabetes mellitus, and it is assumed that it is associated with inadequate setting of the blood sugar level and the associated hyperglycaemia. The higher the blood sugar level and the longer it remains above the norm, the more severe the disease will generally be. The precise mechanism of how increased blood sugar values result in nerve damage still needs to be researched; other factors, such as, for example, anomalies in nerve growth factors or the influence of cardiovascular diseases (ischaemia, hypoxia) have likewise been postulated as important factors which contribute to the development of diabetic neuropathy (see, for example, Jude and Boulton, Diabetes Reviews 1999; 7: 395-410; Dworkin, Clin J Pain 2002; 18: 343-349; Simmons and Feldman, Curr Opin Neurol 2002; 15: 595-603; Barbano et al., Curr Pain Headache Rep 2003; 7: 169-177; Spruce et al., Diabet Med 2003; 20: 88-98).

Surprisingly, it has been found that the derivatives according to the invention can successfully be employed in the diagnosis, prophylaxis and/or treatment of neuropathy, the associated clinical pictures and symptoms and related diseases.

In addition, the derivatives according to the invention preferably accelerate, as described herein, nerve regeneration and therefore particularly preferably accelerate or induce healing of the pathological states or diseases described herein, such as, for example, partial or complete healing of neuropathy. In addition, the derivatives according to the invention preferably exhibit, as described herein, fewer side effects than the pharmaceuticals of the prior art.

The present invention therefore likewise preferably relates to the use of the derivatives according to the invention for the preparation of a medicament for the diagnosis, prophylaxis and/or treatment of neuropathies, the clinical pictures and symptoms associated therewith, and related diseases.

For the purposes of the invention, the neuropathy is preferably selected from diabetes-induced neuropathy, food-induced neuropathy, vitamin-deficiency-induced neuropathy, HIV-induced neuropathy, cancer-induced neuropathy, virus-induced neuropathies, alcohol-abuse-induced neuropathy and medicament-induced neuropathy, particularly preferably diabetes-induced neuropathy, food-induced neuropathy and alcohol-abuse-induced neuropathy, and in particular diabetes-induced neuropathies.

The derivatives according to the invention additionally exhibit high efficacy in neuropathies of other aetiology, and related diseases, clinical pictures or indications, such as, for example, neuralgia after herpes infections, chemotherapy-induced neuropathy, vulvovaginitis; and/or lupus erythematodes. The activity or efficacy of the derivatives according to the invention in the prophylaxis and/or treatment of the said diseases can be demonstrated by methods known from the prior art or analogously thereto, for example as described in Backonja and Glanzman, Clin Ther 2003; 25: 81-104; Bates and Timmins, Int J STD AIDS 2002; 13: 210-212; Carrazana and Mikoshiba, J Pain Symptom Manage 2003; 25(5 Suppl): S31-35; Harel et al., Pediatr Neurol 2002; 27: 53-56; Jensen, Eur J Pain 2002; 6 (Suppl A): 61-68; LaSpina et al. Eur J Neurol 2001; 8: 71-75; Lersch et al., Clin Colorectal Cancer 2002; 2: 54-58; and/or Mellegers et al., Clin J Pain 2001; 17: 284-295), or analogously thereto. The disclosure content of the said publications and the references cited therein is expressly incorporated by way of reference.

The activity or efficacy of the derivatives according to the invention can be determined by processes or methods known from the prior art, or analogously thereto. Suitable methods include experimental non-clinical methods, such as, for example, in-vitro assays, in-vivo assays, cellular assays and animal models, and clinical methods or clinical studies, but are not restricted thereto. Suitable methods are described, for example, in Field et al., Pain 1999; 80: 391-398; Miki et al., Eur J Pharmacol 2001; 430: 229-234; Wallin et al., Eur J Pain 2002; 6: 261-272); Backonja, Epilepsia 1999; 40 (suppl 6): S57-59; Gorson et al., J Neurol Neurosurg Psychiatry 1999; 66: 251-252; Dallocchio et al., J Pain Symptom Manage 2000; 20: 280-285; Hemstreet and Lapointe, Clin Ther 2001; 23: 520-531; Brooks-Rock, Nurse Pract 2001; 26: 59-61; Backonja and Glanzman, Clin Ther 2003; 25: 81-104; Kaul et al., Arch Int Pharmacodyn Ther 1978; 234: 139-44; and Calcutt et al., Anesthesiology 2000; 93: 1271-1278). The disclosure content of the said publications and the references cited therein is expressly incorporated by way of reference.

For example, streptozotocin-induced diabetes in rats is regarded as a suitable animal model for the study of type 1 diabetes (insulin-dependent diabetes) and/or the secondary diseases and the associated symptoms, in particular the secondary diseases described herein and the associated symptoms (see, for example: Kaul et al., Arch Int Pharmacodyn Ther 1978; 234: 139-44; Calcutt et al., Anesthesiology 2000; 93:1271-1278). In this model, even streptozotin-induced chronic diabetes in rats results in sensory disorders, from thermal hypoalgesia to excessive behaviour responses to other sensory stimuli. Malnutrition can increase the sensory nerve defects during diabetes.

In connection with the diagnosis, prophylaxis and/or treatment of neuropathy, the associated clinical pictures and symptoms and the related diseases and in particular the use of the derivatives according to the invention for the preparation of a medicament for use in the diagnosis, prophylaxis and/or treatment of neuropathy, the associated clinical pictures and symptoms and the related diseases, reference is made to the European patent application by the same applicant of Oct. 30, 2003 with the European application number EP 03024781.1 and the secondary international and European applications thereof, the disclosure content of which is incorporated herein in full by way of reference.

The derivatives according to the invention are furthermore suitable for the treatment and/or prophylaxis of pain and oversensitivity to pain, in particular occurring in back complaints, burn injuries, sunburn and rheumatic diseases, and the inflammatory reactions which occur therein. In particular, inflammatory processes in addition to the actual pain and pain oversensitivity reactions in these indications can also be influenced by the administration of suitable pharmaceutical preparations comprising the derivatives according to the invention. The reflex ileus which occurs in the most severe burns can also be prevented or treated. The present invention likewise relates to the use of the derivatives according to the invention for the preparation of a medicament for the treatment and/or prophylaxis of the above-mentioned diseases and/or symptoms.

It has furthermore been found that the derivatives according to the invention indicate an advantageous action in the treatment of allergies, in particular sun allergies, since allergic skin reactions subside rapidly and the itching associated therewith reduces rapidly under the influence of the derivatives according to the invention. Positive results have equally been observed in the treatment of neurodermatitis and in particular pruritus (itching). In particular, the itching of the skin reduces in these diseases under the action of the derivatives according to the invention, and inflammatory skin reactions which occur or are stimulated by the disease are favourably affected. The present invention likewise relates to the use of the derivatives according to the invention for the preparation of a medicament for the treatment and/or prophylaxis of the above-mentioned diseases and/or symptoms. Particular preference is therefore given to the use of the derivatives according to the invention for the prophylaxis and/or treatment of neurodermatitis, itching and in particular pruritus and in particular the use for the preparation of a medicament for the treatment and/or prophylaxis of neurodermatitis, itching and in particular pruritus. In this connection too, the disclosure content of EP-A 0 752 246 is expressly incorporated herein by way of reference.

The derivatives according to the invention are furthermore suitable for the treatment of postoperative pain and pain oversensitivity reactions and the ileus which frequently occurs after abdominal operations. The present invention likewise relates to the use of the derivatives according to the invention for the treatment of and/or for the preparation of a medicament for the treatment of the above-mentioned diseases and/or symptoms.

The derivatives according to the invention can furthermore be employed and are effective for the treatment and/or prophylaxis of non-inflammatory diseases of the gastrointestinal tract, preferably non-inflammatory intestinal diseases and in particular for the treatment and/or prophylaxis of irritable bowel syndrome (IBS) since they can simultaneously ameliorate the pain associated with this disease and cure the disease. It is advantageous here that the derivatives according to the invention have no effects on normal intestinal peristalsis, but play a part in curing irritable bowel syndrome. The derivatives according to the invention can thus advantageously be employed for the prophylaxis of irritable bowel syndrome. In contrast to other compounds having a similar activity spectrum, the derivatives according to the invention and in particular the derivatives of the formula I are particularly suitable for use in pharmaceutical preparations for the treatment of irritable bowel syndrome since, besides the analgesic and antiinflammatory action, they are suitable for normalising the intestinal motor system impairments caused by the disease. In this connection, reference is made to DE 198 49 650, the entire disclosure content of which is incorporated herein by way of reference. The efficacy of the derivatives according to the invention in these indications can be demonstrated by methods known from the prior art, for example as in Delgado-Aros et al., Am. J. Physiol. Gastrointest. Liver Physiol. 284: G558-G566, 2003, or analogously thereto.

The use of the derivatives according to the invention for the treatment and/or prophylaxis of non-inflammatory diseases of the gastrointestinal tract, preferably non-inflammatory intestinal diseases and particularly preferably irritable bowel syndrome, is therefore a preferred aspect of the present invention. The use of the derivatives according to the invention for the preparation of a medicament for the treatment and/or prophylaxis of non-inflammatory diseases of the gastrointestinal tract, preferably non-inflammatory intestinal diseases and particularly preferably irritable bowel syndrome, is therefore a particularly preferred aspect of the present invention.

In addition, the derivatives according to the invention exhibit at least one of the following advantageous properties on administration to patients:

the derivatives according to the invention are effective as modulators of the tonicity of the gastrointestinal tract; in particular, they are suitable for effecting relaxation or activation of the tonicity of the gastrointestinal tract; in general, the modulating action of the derivatives according to the invention is dose-dependent;

the derivatives according to the invention are suitable for influencing the feeling of satiety and/or so-called postprandial symptoms, for example the amount and/or severity of flatulence, the sensation of repletion, nausea and/or pain after ingestion of food;

the effects of the derivatives according to the invention on satiety and/or postprandial symptoms are preferably dose-dependent; in general, low doses result in a decrease in the symptoms, while higher doses can result in an increase in the symptoms;

the derivatives according to the invention can influence the volume, in particular the uptake volume, and/or the tolerance, for example to mechanical stimulation, of the gastrointestinal tract and in particular of the colon; for example, the volume can be significantly increased by the administration of low to moderate doses compared with the state without administration of a derivative according to the invention;

in general, the administration of the derivatives according to the invention exhibits no or slight adverse effects on functional parameters of the gastrointestinal tract, such as, for example, the time of passage through the gastrointestinal tract, gastric emptying, intestinal emptying and colonic emptying; this effect is preferably not or only slightly dose-dependent; the administration of the derivatives according to the invention thus exhibits slight effects on the natural function of the gastrointestinal tract and thus a low tendency towards undesired side effects;

the administration of the derivatives according to the invention in higher doses preferably results in an increase/strengthening of the symptoms relating to the sensation of repletion; for example, patients have the feeling of stomach fullness earlier although they have taken less food and therefore eat less; the derivatives according to the invention can thus be employed for correction of the lack of a sensation of repletion in obese patients and therefore for the treatment of obesity;

the derivatives according to the invention can furthermore be employed and are effective for the treatment and/or prophylaxis of eating disorders and/or digestive disorders, in particular psychogenic eating disorders and/or psychogenic digestive disorders, since they are suitable for advantageously influencing or modulating the tonicity of the gastrointestinal tract.

The derivatives according to the invention are therefore suitable for the treatment and/or prophylaxis of eating and digestive disorders, in particular psychogenic eating and digestive disorders, such as pathologically modified appetite, in particular loss of appetite or reduced appetite, as occurs, for example, in pregnancy, in the case of cancer, in the case of infectious diseases, for example influenza or HIV, as a postoperative side effect, as a consequence of catabolism, cachexia, anorexia, in particular anorexia nervosa, dysorexia, dysponderosis, adipositas polyamine, obesity, gastroparesis, in particular neurogenic gastroparesis, diabetic gastroparesis, myogenic gastroparesis or drug-induced gastroparesis, gastroatonia, gastroparesis solutions or enteroparesis, in particular after gastrointestinal operations, and stenosis of the gastrointestinal tract, in particular stenosis of the pylorus.

The derivatives according to the invention are furthermore suitable for administration as appetite suppressants, individually or in combination with other appetite suppressants, preferably with one or more sympathomimetics. Suitable further appetite suppressants or sympathomimetics are known to the person skilled in the art. Suitable appetite suppressants or sympathomimetics are, in particular, phenylpropanolamine, cathine, sibutramine, amfepramone, ephedrine and norpseudoephedrine. In this connection, reference is made to EP 0 201 1047.4, the full disclosure content of which is incorporated herein by way of reference.

The present invention therefore relates to the use of the derivatives according to the invention for the preparation of a medicament for administration together with appetite suppressants which are different from the derivatives according to the invention. The present invention therefore also relates to the use of the derivatives according to the invention for the preparation of a combination medicament comprising at least one further appetite suppressant.

The dose dependence of the advantageous effects of the derivatives according to the invention on the gastrointestinal tract can be determined easily by conventional methods, for example as described in EP 02011047.4, or analogously thereto. Relatively low doses (in mg of active ingredient, calculated as asimadoline, per kg of body weight) for the purposes of this invention are preferably in the range from 0.001 to 0.5 mg/kg daily, particularly preferably from 0.01 to 1.0 mg/kg daily and in particular from 0.1 to 2.0 mg/kg daily, for example about 0.3 mg/kg daily, about 0.75 mg/kg daily or about 1.0 mg/kg daily, whereas relatively high doses for the purposes of the invention are generally above 2.0 mg/kg daily and preferably in the range from 2.25 to 5 mg/kg daily and in particular in the range from 2.5 mg/kg to 10 mg/kg daily, for example about 3 mg/kg daily, about 5 mg/kg daily or about 8 mg/kg daily.

In addition, there are indications that the derivatives according to the invention can advantageously be employed for the treatment of eye pain, in particular for the topical treatment of eye pain, irrespective of the genesis of the eye pain. The derivatives according to the invention can particularly advantageously be employed for the topical treatment of postoperative eye pain, as can occur, for example, after operations by means of lasers and in particular after so-called PRK operations. PRK here stands for photorefractive keratotomia.

There are furthermore indications that the derivatives according to the invention can advantageously be employed for the treatment of ear pain, in particular for the topical or intranasal treatment of ear pain, irrespective of the genesis of the ear pain. The derivatives according to the invention can particularly advantageously be employed for the treatment of ear pain, as can occur, for example, in otitis, infections, inflammation, in particular middle-ear inflammation, oedema, accident traumas, operations and postoperatively.

The derivatives according to the invention can preferably advantageously be employed for the treatment and/or prophylaxis of dyspepsia, in particular of dyspepsia which is not associated with an ulcer (non-ulcer dyspepsia or NUD).

The derivatives according to the invention can furthermore preferably advantageously be employed for the treatment and/or prophylaxis of neuropathy, in particular diabetic neuropathy.

For the purposes of the invention, diseases or indications are therefore preferably selected from pain, conditions of pain, ear pain, eye pain, inflammation, ileus, inflammatory intestinal diseases, irritable bowel syndrome, irritable bladder syndrome, dyspepsia, neuropathy, adipositas, bulimia, obesity, cachexia, anorexia, dysorexia, dysponderosis, gastroparesis and stenosis of the gastrointestinal tract.

The present invention therefore relates to the use of a derivative according to the invention and/or a salt or solvate thereof for the prevention and/or treatment of diseases, in particular one or more of the diseases or indications mentioned herein.

The present invention therefore preferably relates to the use of a derivative according to the invention and/or a salt or solvate thereof for the preparation of a medicament for the prevention and/or combating of diseases, in particular one or more of the diseases or indications mentioned herein.

In addition, it has proven particularly advantageous in the case of the derivatives according to the invention that, in spite of their advantageously modified property profile as described above, they are apparently unable to cross the blood-brain barrier and therefore have no potential for dependence. In addition, no effects have hitherto been found which would in any way restrict the use of the advantageous actions for the claimed indications. This is particularly surprising since the derivatives according to the invention generally have relatively high, preferably even greatly increased polarity and/or hydrophilicity, which generally greatly increases the ability to cross the blood-brain barrier.

The present invention therefore relates to the use of the derivatives according to the invention for the preparation of a medicament for the treatment and/or prophylaxis of the above-mentioned diseases.

The present invention therefore also relates to a pharmaceutical preparation which comprises at least one of the derivatives according to the invention and/or a solvate or salt thereof. The pharmaceutical preparations according to the invention preferably comprise, based on the total weight of the pharmaceutical preparation, at least 0.001% by weight, particularly preferably at least 0.01% by weight, very particularly preferably at least 0.1% by weight and in particular at least 1.0% by weight of at least one derivative according to the invention and/or a solvate or salt thereof. In general, the preparations according to the invention comprise at most 100% by weight and preferably at most 98% by weight or at most 95% by weight of derivatives according to the invention. In general, the pharmaceutical preparations according to the invention comprise at least 5% by weight, for example at least 15% by weight or at least 30% by weight of further components which are different from the derivatives according to the invention and the salts and solvates thereof, preferably selected from further active ingredients and the conventional constituents, other than active ingredients, which are generally present in pharmaceutical preparations. Examples of further components of this type other than active ingredients are described herein. Examples of further active ingredients of this type which are different from the derivatives according to the invention and the salts and solvates thereof are described herein.

The derivatives according to the invention are preferably prepared in full or in part by conventional chemical synthetic methods, biotechnological methods or genetic engineering methods. In the preparation of the derivatives according to the invention, at least the covalent bonding between the N-methyl-N-[(1S)-1-phenyl-2-((3S)-3-hydroxypyrrolidin-1-yl)ethyl]-2,2-diphenylacetamide and the covalently bonded acid is preferably carried out by means of conventional chemical synthetic methods. A suitable conventional chemical synthetic method is described below.

The invention furthermore relates to a process for the preparation of the derivatives according to the invention and physiologically acceptable salts thereof, characterised in that
a) a compound of the formula II

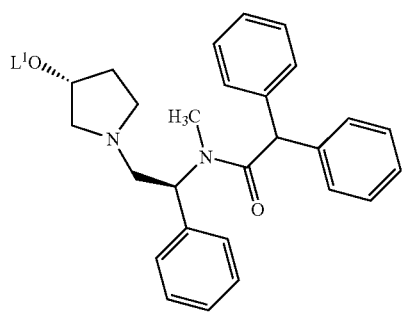

II in which
L$^1$ is H or a metal ion;
b) is reacted with a compound of the formula III

R$^1$-L$^2$      III in which
L$^2$ is a leaving group, preferably selected from Cl, Br, I, OH, SR$^3$, a reactively esterified OH group, an imidazolide group, a carboxylate group and a diazonium group, R$^3$ is alkyl, aralkyl or aryl, and R$^1$ is as defined above and below for the compounds of the formula or, if R$^1$ contains one or more functional groups, preferably one or more functional groups, selected from hydroxyl groups and carboxyl groups, in addition to the group L$^2$,
a derivative of R$^1$ which is provided fully or partly with protecting groups,
c) where appropriate, one or more protecting groups are cleaved off from R$^1$ if the product of the reaction of a) and b) contains one or more protecting groups; if desired, the compound of the formula I is isolated,
d) the resultant compound of the formula I is converted into one of its salts by treatment with an acid or base, and, if desired, the salt is isolated.

In the compounds of the formula II, L$^1$ is preferably H or a metal ion. Suitable metal ions are, in particular, alkali metal, alkaline earth metal or aluminium ions. Preferred metal ions are alkali metal ions, in particular Li, Na or K. L$^1$ is particularly preferably H.

In the compounds of the formula III, R$^1$ is preferably selected from
a) acyl radicals, as described above for the compounds of the formula I
b) acyl radicals which contain a hydroxyl group and/or one or more carboxyl groups, as described above for the compounds of the formula I,
c) alkyl radicals derived from polyhydroxymonocarboxylic acids, as described above for the compounds of the formula I, and
d) sulfonic acid groups, phosphonic acid groups and nitro groups as described above for the compounds of the formula I.

In the compounds of the formula III, L$^2$ is a suitable leaving group. Suitable leaving groups are known to the person skilled in the art, for example from Houben-Weyl, Methoden der organischen Chemie [Methods of Organic Chemistry], Thieme-Verlag, Stuttgart. Besides the halides F, Cl, Br and I and reactively esterified OH groups, examples of suitable leaving groups are in particular imidazolides, acid anions derived from acid anhydrides, as formed, for example, if the compound of the formula III employed is a mixed or asymmetrical or symmetrical acid anhydride, and diazonium groups, as can be obtained, for example, by diazotisation of amines by conventional methods.

For the purposes of the invention, reactively esterified OH groups are preferably alkylsulfonyloxy groups having 1-6 carbon atoms (preferably methylsulfonyloxy) or arylsulfonyloxy groups having 6-10 carbon atoms (preferably phenyl- or p-tolylsulfonyloxy).

In many cases, the compound of the formula III advantageously employed in the process according to the invention is an acid halide, preferably an acid halide derived from the above-mentioned acids. Suitable acid halides of the above-mentioned acids and processes for their preparation are known to the person skilled in the art. The acid halide is preferably chlorosulfonic acid.

In many cases, the compound of the formula III advantageously employed in the process according to the invention is an acid anhydride, preferably an acid anhydride which is derived from the above-mentioned acids or contains at least one of the acids mentioned above/below for the preparation of the derivatives according to the invention. Suitable acid anhydrides for the preparation of the derivatives according to the invention by the process according to the invention are known to the person skilled in the art. The acid anhydride is preferably acetic anhydride.

In the compounds of the formula III, L$^2$ is preferably selected from Cl, Br and SR$^3$ and is in particular Br.

In the compounds of the formula III, $L^2$ is preferably not OH and/or a diazonium group.

In the compounds of the formula III in which $L^2$ is $SR^3$, $R^3$ is preferably selected from branched or unbranched alkyl radicals having from 1 to 10 carbon atoms, such as, preferably, methyl, ethyl, n-propyl, isopropyl, n-butyl, isobutyl, tert-butyl, in particular ethyl, aralkyl radicals having from 6 to 10 carbon atoms, such as benzyl, and aryl radicals having from 6 to 10 carbon atoms, such as phenyl, p-nitrophenyl and p-tolyl. Particular preference is given to methyl, ethyl, isopropyl, n-butyl, isobutyl, phenyl and benzyl. Preferred groups $SR^3$ are selected from S—$C_2H_5$, S—$CH(CH_3)_2$, S—$C_6H_5$ and S.$CH_2$—$C_6H_5$.

The process according to the invention can be carried out in the absence or presence, preferably in the presence, of a suitable solvent, preferably one which is inert under the reaction conditions. Suitable solvents are known to the person skilled in the art. Preferred solvents, in particular for reaction steps a) and b), are polar, aprotic solvents, such as acetonitrile, tetrahydrofuran (THF), 1,4-dioxane and dichloromethane. Particularly suitable solvents for reaction steps c) and/or d) are the solvents which have been proposed for the removal of the respective protecting group.

The reaction times for the process according to the invention are generally between a few minutes and a few days, preferably between 30 minutes and 48 hours and in particular between one hour and 24 hours.

The reaction temperatures for the process according to the invention are generally between –20° C. and 100° C., preferably between –10° C. and 60° C., particularly preferably between 0° C. and 40° C., for example about room temperature (25° C.).

The process according to the invention can be carried out in the presence of adjuvants which positively influence the reaction rate, the selectivity and/or the yield of the process according to the invention. Examples of assistants of this type are auxiliary bases, catalysts and substances which remove at least one of the resultant products and/or by-products from the process. Suitable assistants of this type are known to the person skilled in the art, for example from Houben-Weyl, Methoden der organischen Chemie [Methods of Organic Chemistry].

If use is made of a compound of the formula III in which $L^2$ is halogen and in particular chlorine or bromine, it may be advantageous, when carrying out the process according to the invention, to add a silver salt which removes the halide liberated during the reaction according to the invention of the compound of the formula II with a compound of the formula III from the process in the form of a low-solubility precipitate. Suitable silver salts are known to the person skilled in the art, for example silver nitrate, silver carbonate and silver perchlorate. The silver salt is preferably silver perchlorate.

If use is made of a compound of the formula III in which $L^2$ is $SR^3$, it may be advantageous when carrying out the process according to the invention to add an N-halosuccinimide, in particular N-iodosuccinimide, and/or a halocarboxylic acid, in particular trifluoroacetic acid.

If the radical $R^1$ in the compound of the formula III contains further functional groups (in addition to the group $L^2$), in particular further hydroxyl groups and/or acid groups, it is in many cases advantageous to employ a so-called protected derivative, i.e. a derivative provided with one or more protecting groups, of a radical $R^1$ as described above in the process according to the invention. The further functional groups here are advantageously protected by means of the usual protecting groups for the respective functional group. Suitable protecting groups and processes for the preparation of protected derivatives of this type are known to the person skilled in the art. Hydroxyl groups are preferably protected with hydroxyl-protecting groups, acid groups preferably with acid-protecting groups.

The term "hydroxyl-protecting group" is known in general terms and relates to groups which are suitable for protecting a hydroxyl group against chemical reactions, but which are easily removable after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are generally removed again after the desired chemical reaction or reaction sequence; preference is given to groups having 1-20, in particular 1-10, carbon atoms. Examples of hydroxyl-protecting groups are, inter alia, benzyl, p-nitrobenzoyl, p-toluenesulfonyl, tert-butyl and acetyl, where acetyl, benzyl and tert-butyl and especially acetyl are particularly preferred. Protected hydroxyl groups are thus generally in the form of ether groups and/or ester groups.

The term "acid-protecting group" is likewise known in general terms and relates to groups which are suitable for protecting an acid group, preferably a carboxylic acid group or an acid group of an inorganic oxygen acid, in particular the acid groups of the above-mentioned acids, against chemical reactions, but which are easily removable after the desired chemical reaction has been carried out elsewhere in the molecule. Typical of such groups are unsubstituted or substituted, preferably unsubstituted aryl, aralkyl or alkyl groups. Protected acid groups are thus preferably in the form of the aryl, aralkyl or alkyl esters, particularly preferably aralkyl or alkyl esters, of the said acid groups. Preferred acid-protecting groups are the methyl group, the tert-butyl group and the benzyl group, particularly preferably the methyl group. Esters can, for example, be saponified using acetic acid or using NaOH or KOH in water, water/THF or water/dioxane at temperatures between 0 and 100°.

The liberation of the protected derivatives according to the invention and in particular protected compounds of the formula I is carried out—depending on the protecting group used—either using acids, preferably strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid, or bases, preferably strong bases, such as amines, alkali metal hydroxides, alkaline earth metal hydroxides, alkali metal carbonates and alkaline earth metal carbonates, preferably sodium hydroxide, potassium hydroxide, sodium carbonate or potassium carbonate. The base is preferably sodium hydroxide, for example an aqueous sodium hydroxide solution. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Also suitable are mixtures of the above-mentioned solvents. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30°, for example room temperature.

Esters and/or ethers can, for example, advantageously be saponified using acetic acid or in particular using NaOH or KOH in water, water/THF or water/dioxane at temperatures between 0 and 100°, preferably at about room temperature (25° C.).

Hydrogenolytically removable protecting groups (for example benzyl) can be cleaved off, for example, by treatment with hydrogen or a hydrogen-liberating compound, for example ammonium formate, in the presence of a catalyst (for example a noble-metal catalyst, such as palladium, advantageously on a support, such as carbon). Suitable solvents here are solvents as are usually used in hydrogenations, in particular, for example, alcohols, such as methanol or ethanol, ethers, such as diethyl ether, tetrahydrofuran (THF) or 1,4-dioxane, or amides, such as DMF. The hydrogenolysis is generally carried out at temperatures between about 0 and 100° and pressures between about 1 and 200 bar, preferably at 20-30° C. and 1-10 bar.

The protected compound of the formula III, i.e. the compound of the formula III provided with one or more protecting groups, is particularly preferably a compound of the formula IIIa or IIIb

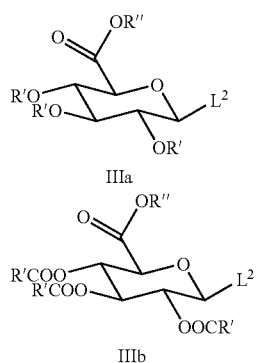

in which each radical R' and R", independently of one another, is selected from H, branched and unbranched alkyl radicals having from 1 to 10 carbon atoms, aralkyl radicals having from 6 to 10 carbon atoms and aryl radicals having from 6 to 10 carbon atoms, preferably methyl, ethyl, n-propyl, isopropyl, n-butyl, isobutyl, tert-butyl, benzyl, p-nitrophenyl and p-tolyl, particularly preferably methyl, benzyl and tert-butyl and in particular methyl, with the proviso that at least one of the radicals R' and R" is not H. Preferably, a plurality of the radicals R' and R" and in particular all radicals R' and R" are not H. Very particular preference is given to compounds of the formula IIIb in which R' and R" are methyl.

The protected compound of the formula III, i.e. the compound of the formula III provided with one or more protecting groups, is therefore particularly preferably a compound of the formula IIIc

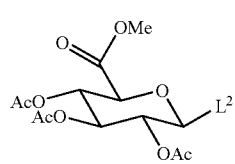

in which the abbreviation Ac is an acetyl radical, and Me is a methyl group. In the formulae IIIa, IIIb and IIIc, $L^2$ is preferably Br.

Compounds of the formula III in which $L^2$ is $SR^3$ or S—C(O)—$R^3$ can be obtained by known methods. For example, they can be prepared by the method described by Arie L. Gutman et al., Synthesis 2000, 1241-1246, or analogously thereto.

The protected compound of the formula III, i.e. the compound of the formula III provided with one or more protecting groups, is therefore likewise preferably a compound of the formula IIId or IIIe

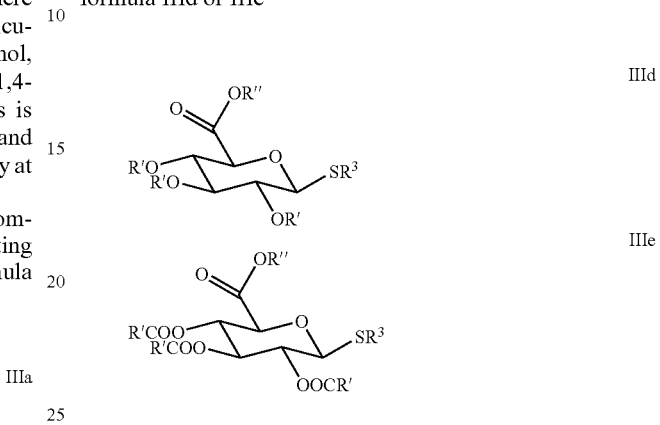

in which R' and $R^3$ are as defined above, and in particular in which R' in the formula IIId is benzyl and R' in the formula IIIe is isopropyl. $R^3$ is preferably ethyl or phenyl.

Compounds of the formula IIId or IIIe can be obtained, for example, starting from compounds of the formula IIIa or IIIb and in particular from compounds of the formula IIIc, in particular those in which $L^2$ is halogen, where, in a first step, a radical $L^2$ which is not $SR^3$ is converted into a radical $L^2$ which is $SR^3$, for example by substitution and in particular by nucleophilic substitution.

The process according to the invention can be carried out as a one-pot reaction, i.e. isolation and/or purification steps are omitted as far as possible and only the desired end product, i.e. generally a derivative according to the invention or a protected derivative thereof, preferably a derivative according to the invention and in particular a compound of the formula I, is purified and/or isolated. Alternatively, a purification and/or isolation step can be carried out after each of the said reaction steps. Mixed forms of the procedure described above are also conceivable.

Suitable purification and isolation steps are known to the person skilled in the art, for example from Houben-Weyl, Methoden der organischen Chemie [Methods of Organic Chemistry].

If, as in process step b) of the process according to the invention described above, use is made of a compound of the formula III in which $R^1$ is in the form of a derivative which is provided fully or partly with protecting groups, but use is made of the option under process step c) and the protecting groups of $R^1$ are not cleaved off or are not cleaved off completely, a derivative according to the invention is obtained which contains one or more protecting groups. Alternatively, a derivative according to the invention which contains one or more protecting groups can also be obtained by providing one or more of the functional groups in a derivative according to the invention which contains at least one further functional group, preferably selected from hydroxyl groups, acid functions which are capable of salt formation and acid functions in the form of a salt, with a protecting group. Derivatives according to the invention as described above which contain at least one protecting group or a functional group which is provided with a protecting group are referred to below as protected derivatives.

For the purposes of this invention, protected derivatives are therefore taken to mean, in particular, derivatives according to the invention in which the covalently bonded acid contains one or more further functional groups, in particular hydroxyl and/or acid groups, in which one or more of the further functional groups are protected as described above, i.e. is provided with a protecting group. Further functional groups for the purposes of this invention are the functional groups and in particular the hydroxyl and/or acid groups of the acids covalently bonded in accordance with the invention which do not effect the covalent bond to the N-methyl-N-[(1S)-1-phenyl-2-((3S)-3-hydroxypyrrolidin-1-yl)ethyl]-2,2-diphenylacetamide radical.

Examples of preferred protected derivatives are derivatives according to the invention in which the further functional groups are in the form of one or more hydroxyl and/or one or more acid groups, where all or some of the hydroxyl groups are in acetalated form and/or all or some of the acid groups are in the form of the alkyl esters and in particular the methyl esters.

Preferred protected derivatives, i.e. derivatives provided with one or more protecting groups, are compounds of the formula Iaa

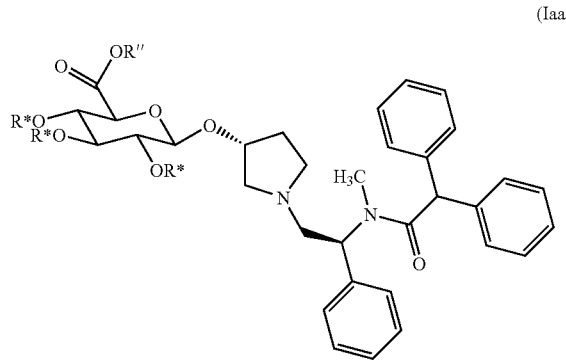

(Iaa)

and compounds of the formula Ibb

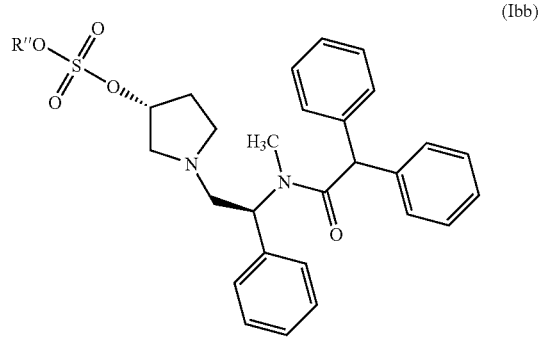

(Ibb)

in which all radicals R* are selected, independently of one another, from H and R'CO, and the radicals R' and R" are as defined above, with the proviso that at least one of the radicals R*, R' and R" in each of the compound of the formula Iaa and the compound of the formula Ibb is not H, and the salts and solvates thereof.

Very particularly preferred protected derivatives are the compounds of the formula Iaa and the salts and solvates thereof.

For the purposes of this invention, protected derivatives are preferably those in which all radicals R*, R' and R" are not H or, if two or more radicals selected from R*, R' and R" are present, those in which only one or two of the radicals R*, R' and R" are H and preferably those in which only one of the radicals R*, R' and R" is H.

The derivatives according to the invention interact, as described above, intensively with the organism, in particular the enterohepatic circulation. Experiments have shown that protected derivatives as described above can also be modified in full or part into derivatives according to the invention or converted into the latter under physiological conditions, for example by interactions as described above. Thus, protected derivatives can be regarded as having an equivalent action to the derivatives according to the invention and thus as prodrugs in the sense of this invention. The present invention thus also relates to the protected derivatives which can be employed, as described below, as active ingredient for the treatment of diseases and in particular for the preparation of medicaments and/or pharmaceutical preparations.

Preferred prodrugs are protected derivatives in which the covalently bonded acid is selected from dibasic carboxylic acids and monobasic hydroxycarboxylic acids. Preferred monobasic hydroxycarboxylic acids in this sense are sugar acids.

Particularly preferred prodrugs are derivatives according to the invention in which the covalently bonded acid is selected from sugar acids and in which one or more of the further functional groups as described above contain a protecting group as described above. Particularly preferred prodrugs are derivatives according to the invention in which all or some of the hydroxyl groups are in acetalated form and/or in which all or some of the acid groups are in the form of the alkyl esters and in particular the methyl esters.

The compounds of the general formula I and physiologically acceptable salts thereof can therefore be used for the preparation of pharmaceutical preparations by converting them into a suitable dosage form together with at least one excipient or adjuvant and, if desired, with one or more further active ingredients.

The present invention therefore relates to a process for the preparation of pharmaceutical compositions as described above and in particular to a process for the preparation of pharmaceutical preparations in which at least one derivative according to the invention and at least one further compound selected from excipients, adjuvants and pharmaceutical active ingredients which are different from derivatives according to the invention are converted, using one or more mechanical process steps, into a pharmaceutical composition which is suitable as dosage form for administration to patients. Suitable mechanical process steps are known to the person skilled in the art and include, inter alia, mixing processes, grinding processes, dissolution processes, sieving processes, homogenisation, drying, pressing, tabletting, coating and/or sugar-coating.

The present invention therefore also relates to the pharmaceutical compositions obtainable by this process.

For the purposes of the invention, suitable dosage forms are preferably tablets, coated tablets, capsules, syrups, juices, drops, suppositories, plasters, solutions, in particular parenteral solutions, suspensions, creams, ointments, emulsions and implants which comprise at least one derivative according to the invention and/or a salt or solvate thereof.

The invention therefore also relates to a pharmaceutical preparation characterised by a content of at least one derivative according to the invention and/or one of its salts, in particular physiologically acceptable salts, as described above, and in particular pharmaceutical preparations as described above for the treatment and/or prophylaxis of one or more of the diseases described above.

The present invention also relates to a pharmaceutical preparation comprising at least one derivative according to the invention and/or a salt or solvate thereof and at least one further active ingredient which is different from the derivatives according to the invention and is preferably also different from N-methyl-N-[(1S)-1-phenyl-2-((3S)-3-hydroxypyrrolidin-1-yl)ethyl]-2,2-diphenylacetamide.

The present invention also relates to a pharmaceutical preparation comprising at least one derivative according to the invention and/or a salt or solvate thereof and at least one further active ingredient, preferably an active ingredient which acts as appetite suppressant.

The preparations obtained in this way can be employed as medicaments in human or veterinary medicine. Suitable carrier substances are organic or inorganic substances which are suitable for enteral (for example oral or rectal) or parenteral administration and do not react with the novel compounds, for example water, vegetable oils, benzyl alcohols, polyethylene glycols, glycerol triacetate and other fatty acid glycerides, gelatine, soya lecithin, carbohydrates, such as lactose or starch, magnesium stearate, talc or cellulose.

Suitable for oral administration are, in particular, tablets, coated tablets, capsules, syrups, juices or drops. Of particular interest are film-coated tablets and capsules having gastric juice-resistant coatings or capsule shells. Suitable for rectal administration are suppositories, and suitable for parenteral administration are solutions, preferably oil-based or aqueous solutions, furthermore suspensions, emulsions or implants.

The active ingredients claimed in accordance with the invention may also be lyophilised and the resultant lyophilisates used, for example, for the preparation of injection preparations.

The preparations mentioned may be sterilised and/or comprise adjuvants, such as preservatives, stabilisers and/or wetting agents, emulsifiers, salts for modifying the osmotic pressure, buffer substances, colorants and/or aroma substances. They may, if desired, also comprise one or more further active ingredients, for example one or more vitamins, diuretics or antiphlogistics.

The derivatives according to the invention are generally administered analogously to other known preparations which are commercially available for the claimed indications, preferably in doses of between about 1 mg and 70 mg, in particular between 5 and 50 mg per dosage unit. The daily dose is preferably between about 0.02 and 30 mg/kg, in particular between 0.2 and 0.6 mg/kg of body weight.

However, the specific dose for each individual patient depends on a very wide variety of factors, for example on the efficacy of the specific compound employed, on the age, body weight, general state of health, sex, on the diet, on the time and method of administration, on the excretion rate, medicament combination and severity of the particular disease to which the therapy applies. Oral administration is preferred.

EXAMPLES

Preparation of 6-(1-{[(2,2-diphenylethanoyl)methylamino]phenylethyl}pyrrolidin-3-yloxy)-3,4,5-trihydroxytetrahydropyran-2-carboxylic acid (Compound Ia)

a) A mixture of 2.0 g (4.434 mmol) of N-methyl-N-[(1S)-1-phenyl-2-((3S)-3-hydroxypyrrolidin-1-yl)ethyl]-2,2-diphenylacetamide and 1.76 g (4.430 mmol) of glycosyl halide A is initially introduced in 50 ml of acetonitrile, an excess of a silver salt, for example silver perchlorate or silver carbonate, is added, and the reaction mixture is stirred overnight at room temperature. After filtration through kieselguhr, the solvent is removed under reduced pressure, and the residue is purified by chromatography (flash chromatography on SI-60 with toluene/methanol=9:1→4:1 as eluent; $R_f$=0.54, toluene/MeOH 4:1), giving 190 mg of compound B.

b) 110 mg (0.151 mmol) of compound B are dissolved in 4 ml of 1,4-dioxane, 0.755 ml of 1N sodium hydroxide solution is added, and the mixture is stirred at room temperature. Monitoring of the reaction by HPLC shows that the reaction is complete after stirring for about three hours. The reaction mixture is subsequently neutralised using 1N hydrochloric acid and evaporated to dryness. The resultant residue can be purified by preparative HPLC on RP-18, giving 65 mg of compound (Ia) ($R_t$=31.65 min (Lichrospher 1000, RP-18, 5 µm, gradient elution (A:B from 99:1 to 1:99 in 1 hour; A: $H_2O$+0.3% TFA (=trifluoroacetic acid); B: $CH_3CN/H_2O$ (80:20)+0.3% TFA).

Alternatively, the synthesis can be carried out as a one-pot reaction in which chromatographic purification of the reaction product from step a) is omitted. In this case, the reaction mixture is filtered when the reaction is complete, and the solvent is removed under reduced pressure. If desired after the resultant residue has been taken up in water and extracted with dichloromethane or methyl acetate, sodium hydroxide solution can be added, as described in step b), and the mixture is stirred at room temperature. The resultant crude product of 6-(1-{[(2,2-diphenylethanoyl)methylamino]phenylethyl}pyrrolidin-3-yloxy)-3,4,5-trihydroxytetrahydropyran-2-carboxylic acid can be worked up as described under step b).

Preparation of mono-{1-[2-(diphenylacetylmethylamino)-2-phenylethyl]pyrrolidin-3-yl}sulfate (Ib)

0.9 gram (2.0 mmol) of N-methyl-N-[(1S)-1-phenyl-2-((3S)-3-hydroxypyrrolidin-1-yl)ethyl]-2,2-diphenylacetamide is initially introduced in 10 ml of dichloromethane, and 150 µl (2.0 mmol) of chlorosulfonic acid are added. After a reaction time of two days, the solvent is distilled off, the resultant residue is triturated a number of times with acetone and the supernatant acetone decanted off, and the resultant crystals are filtered off under reduced pressure and dried in air. Drying in air gives 740 mg (74.3% of theory) of crystalline solid of compound (Ib) having a melting point of 268° C.

Preparation of N-{2-[(3S)-3-acetoxy-1-pyrrolidinyl]-(1S)-1-phenylethyl}-2,2-diphenyl-N-methylacetamide (Compound Ic)

30 ml of acetic anhydride and 15 ml of triethylamine are added to 5.0 grams (11.0 mmol) of N-methyl-N-[(1S)-1-phenyl-2-((3S)-3-hydroxypyrrolidin-1-yl)ethyl]-2,2-diphenylacetamide, hydrochloride, and the mixture is heated for two hours on a steam bath. The reaction mixture is subsequently evaporated to dryness, and the residue is taken up in ether and washed with bicarbonate solution. The organic phase is subsequently dried, and the solvent is distilled off. The resultant residue is purified by column chromatography on silica gel with diethyl ether/methanol (99:1) as eluent. The resultant crude product of N-{2-[(3S)-3-acetoxy-1-pyrrolidinyl]-(1S)-1-phenylethyl}-2,2-diphenyl-N-methylacetamide can be purified further by taking up in diethyl ether, precipitation by addition of ethereal HCl, filtering-off of the resultant crystals under reduced pressure, washing of the crystals with ether and drying in air ($R_f$=0.6 (TLC on silica gel 6 $F_{254}$ with dichloromethane/methanol (8:2) as eluent)).

The invention claimed is:

1. A method of treating a subject having irritable bowel syndrome, comprising administering an effective dose of N-methyl-N-[(1S)-1-phenyl-2-((3S)-3-hydroxy-pyrrolidin-1-yl)ethyl]-2,2-diphenylacetamide covalently bonded to at least one acid, and/or a salt of N-methyl-N-[(1S)-1-phenyl-2-((3S)-3-hydroxy-pyrrolidin-1-yl)ethyl]-2,2-diphenylacetamide covalently bonded to at least one acid, to a subject having irritable bowel syndrome, thereby treating irritable bowel syndrome.

2. A method of treating a subject having functional diarrhea, comprising administering an effective dose of N-methyl-N-[(1S)-1-phenyl-2-((3S)-3-hydroxy-pyrrolidin-1-yl)ethyl]-2,2-diphenylacetamide covalently bonded to at least one acid, and/or a salt of N-methyl-N-[(1S)-1-phenyl-2-((3S)-3-hydroxy-pyrrolidin-1-yl)ethyl]-2,2-diphenylacetamide covalently bonded to at least one acid, to a subject having functional diarrhea, thereby treating functional diarrhea.

3. A method of treating a subject having post-operative ileus, comprising administering an effective dose of N-methyl-N-[(1S)-1-phenyl-2-((3S)-3-hydroxy-pyrrolidin-1-yl)ethyl]-2,2-diphenylacetamide covalently bonded to at least one acid, and/or a salt of N-methyl-N-[(1S)-1-phenyl-2-((3S)-3-hydroxy-pyrrolidin-1-yl)ethyl]-2,2-diphenylacetamide covalently bonded to at least one acid, to a subject having post-operative ileus, thereby treating post-operative ileus.

4. The method of claim 1, wherein the acid is covalently bonded via the 3-hydroxypyrrolidine group of N-methyl-N-[(1 S)-1phenyl-2-((3S)-3-hydroxypyrrolidin-1-yl)ethyl]-2,2-diphenylacetamide.

5. The method of claim 1, wherein the acid is a carboxylic acid, hydroxycarboxylic acid or inorganic oxygen acid.

6. The method of claim 1, wherein the acid is a dibasic carboxylic acid, monobasic hydroxycarboxylic acid, or dibasic inorganic oxygen acid.

7. The method of claim 6, wherein the monobasic hydroxycarboxylic acid is a sugar acid.

8. The method of claim 7, wherein the sugar acid is glucuronic acid.

9. The method of claim 6, wherein the dibasic inorganic oxygen acid is sulfuric acid.

10. The method of claim 1, wherein 6-(1-{[(2,2diphenylethanoyl)methylamino]phenylethyl} pyrrolidin-3-yloxy}-3,4,5-tri-hydroxytetrahydropyrarr-2-carboxylic acid, mono-{1[2-(diphenylacetyl-methylamino)-2phenylethyl]pyrrolidin-3-yl} sulfate, N-{2-[(3S)-3-acetoxy-1-pyrrolidinyl]-(1S)-1-phenylethyl}-2,2-diphenyl-N-methylacetamide, or a salt thereof is administered.

11. A method of treating irritable bladder syndrome, comprising administering an effective dose of N-methyl-N-[(1S)-1-phenyl-2-((3S)-3-hydroxy-pyrrolidin-1-yl)ethyl]-2,2-diphenylacetamide covalently bonded to at least one acid, and/or a salt of N-methyl-N-[(1S)-1-phenyl-2-((3S)-3-hydroxy-pyrrolidin-1-yl)ethyl]-2,2-diphenylacetamide covalently bonded to at least one acid to a subject having irritable bladder syndrome, thereby treating irritable bladder syndrome.

12. The method of claim 11, wherein the acid is covalently bonded via the 3-hydroxypyrrolidine group of N-methyl-N-[(1 S)-1phenyl-2-((3S)-3-hydroxypyrrolidin-1-yl)ethyl]-2,2-diphenylacetamide.

13. The method of claim 11, wherein the acid is a carboxylic acid, hydroxycarboxylic acid or inorganic oxygen acid.

14. The method of claim 11, wherein the acid is a dibasic carboxylic acid, monobasic hydroxycarboxylic acid, or dibasic inorganic oxygen acid.

15. The method of claim 14, wherein the monobasic hydroxycarboxylic acid is a sugar acid.

16. The method of claim 15, wherein the sugar acid is glucuronic acid.

17. The method of claim 14, wherein the dibasic inorganic oxygen acid is sulfuric acid.

18. The method of claim 11, wherein 6-(1-{[(2,2diphenylethanoyl)methylamino]phenylethyl} pyrrolidin-3-yloxy}-3,4,5-tri-hydroxytetrahydropyrarr-2-carboxylic acid, mono-{1[2-(diphenylacetyl-methylamino)-2phenylethyl]pyrrolidin-3-yl} sulfate, N-{2-[(3S)-3-acetoxy-1-pyrrolidinyl]-(1S)-1-phenylethyl}-2,2-diphenyl-N-methylacetamide, or a salt thereof is administered.

19. The method of claim 2, wherein the acid is covalently bonded via the 3-hydroxypyrrolidine group of N-methyl-N-[(1 S)-1phenyl-2-((3S)-3-hydroxypyrrolidin-1-yl)ethyl]-2,2-diphenylacetamide.

20. The method of claim 2, wherein 6-(1-{[(2,2diphenylethanoyl)methylamino]phenylethyl} pyrrolidin-3-yloxy}-3,4,5-tri-hydroxytetrahydropyrarr-2-carboxylic acid, mono-{1[2-(diphenylacetyl-methylamino)-2phenylethyl]pyrrolidin-3-yl} sulfate, N-{2-[(3S)-3-acetoxy-1-pyrrolidinyl]-(1S)-1-phenylethyl}-2,2-diphenyl-N-methylacetamide, or a salt thereof is administered.

21. The method of claim 3, wherein the acid is covalently bonded via the 3-hydroxypyrrolidine group of N-methyl-N-[(1 S)-1phenyl-2-((3S)-3-hydroxypyrrolidin-1-yl)ethyl]-2,2-diphenylacetamide.

22. The method of claim 3, wherein the acid is a carboxylic acid, hydroxycarboxylic acid or inorganic oxygen acid.

23. The method of claim 3, wherein 6-(1-{[(2,2diphenylethanoyl)methylamino]phenylethyl} pyrrolidin-3-yloxy}-3,4,5-tri-hydroxytetrahydropyrarr-2-carboxylic acid, mono-{1[2-(diphenylacetyl-methylamino)-2phenylethyl]pyrrolidin-3-yl} sulfate, N-{2-[(3S)-3-acetoxy-1-pyrrolidinyl]-(1S)-1-phenylethyl}-2,2-diphenyl-N-methylacetamide, or a salt thereof is administered.

* * * * *